US008871180B2

(12) United States Patent
Kataoka et al.

(10) Patent No.: US 8,871,180 B2
(45) Date of Patent: Oct. 28, 2014

(54) ORGANIC-INORGANIC HYBRID PARTICLES CONTAINING CONTRAST AGENT

(75) Inventors: Kazunori Kataoka, Tokyo (JP); Michiaki Kumagai, Tokyo (JP); Keisuke Aikawa, Misato (JP)

(73) Assignee: Japan Science and Technology Agency, Saitama (JP)

( * ) Notice: Subject to any disclaimer, the term of this patent is extended or adjusted under 35 U.S.C. 154(b) by 1310 days.

(21) Appl. No.: 12/734,808

(22) PCT Filed: Sep. 4, 2007

(86) PCT No.: PCT/JP2007/067556
§ 371 (c)(1),
(2), (4) Date: May 25, 2010

(87) PCT Pub. No.: WO2008/068939
PCT Pub. Date: Jun. 12, 2008

(65) Prior Publication Data
US 2010/0278737 A1  Nov. 4, 2010

(30) Foreign Application Priority Data

Dec. 7, 2006  (JP) ................................. 2006-330436

(51) Int. Cl.
| | |
|---|---|
| *A61K 49/00* | (2006.01) |
| *B32B 7/02* | (2006.01) |
| *B32B 9/00* | (2006.01) |
| *C08L 53/00* | (2006.01) |
| *A61K 49/12* | (2006.01) |
| *A61K 49/18* | (2006.01) |
| *A61K 49/10* | (2006.01) |
| *C08K 3/26* | (2006.01) |
| *C08K 3/32* | (2006.01) |

(52) U.S. Cl.
CPC .............. *A61K 49/1824* (2013.01); *C08K 3/26* (2013.01); *C08L 53/00* (2013.01); *C08K 3/32* (2013.01); *A61K 49/126* (2013.01); *A61K 49/105* (2013.01)
USPC ............. 424/9.1; 428/216; 428/221; 428/407

(58) Field of Classification Search
None
See application file for complete search history.

(56) References Cited

U.S. PATENT DOCUMENTS

| | | | |
|---|---|---|---|
| 2002/0197261 A1* | 12/2002 | Li et al. ....................... | 424/178.1 |
| 2003/0224038 A1* | 12/2003 | Page et al. ...................... | 424/450 |
| 2004/0185113 A1* | 9/2004 | Mizushima et al. .......... | 424/490 |
| 2004/0197360 A1 | 10/2004 | Kataoka et al. | |
| 2008/0241073 A1 | 10/2008 | Yokoyama et al. | |

FOREIGN PATENT DOCUMENTS

| | | |
|---|---|---|
| WO | 03/018690 | 3/2003 |
| WO | 2006/003731 | 1/2006 |

OTHER PUBLICATIONS

International Preliminary Report on Patentability issued Jun. 10, 2009 in International Application No. PCT/JP2007/067556.
International Search Report issued Jan. 8, 2008 in International Application No. PCT/JP2007/067556.
P. Caravan, et al., "Gadolinium (III) Chelates as MRI Contrast Agents: Structure, Dynamics, and Applications", Chem. Rev. 1999, vol. 99, p. 2293-2352.
V. Jacques, et al., "New Classes of MRI Contrast Agents" Topics in Current Chemistry (Springer-Verlag), Contrast Agents 1, Magnetic Resonance Imaging, Edited by Werner Krause, 2002, vol. 221, p. 123-164.
D.D. Schwert, et al., "Non-Gadolinium-Based MRI Contrast Agents" Topics in Current Chemistry (Springer-Verlag), Contrast Agents 1, Magnetic Resonance Imaging, Edited by Werner Krause, 2002, vol. 221, p. 165-199.
M. Kumagai et al., "Organic-inorganic hybrid-nanocarrier of Gd-DTPA constructing through the self-assembly of calcium phosphate and PEG-based block aniomer as pH-responsive MRI contrast agent", Polymer Preprints, Japan (CD-ROM), Sep. 25, 2006 vol. 55, No. 2, 3 Pa 111.
H. Cölfen et al., "A systematic examination of the Morphogenesis of Calcium Carbonate in the Presence of a Double-Hydrophilic Block Copolymer", Chemistry, Jan. 5, 2001, vol. 7, No. 1, p. 106-116, p. 107, left column, line 42 to right column, line 15, Fig. 1(c).
J. Bolze et al., Time-resolved SAXS study of the effect of a double hydrophilic block-copolymer on the formation of $CaCO_3$ from a supersaturated salt solution, Journal of Colloid and Interface Science, Sep. 1, 2004, vol. 277, No. 1, p. 84-94, p. 88, left column, line 23, to right column, line 18, Fig. 3.
M. Kumagai et al., "Organic-inorganic hybrid-nanocarrier of Gd-DTPA constructing through the self-assembly of calcium carbonate and PEG-based block aniomer as pH-responsive MRI contrast agent", the Annual Meeting of the Japanese Society for Biomaterials Yokoshu, Nov. 27, 2006, vol. 28, p. 275, JDreamII [on line]; Japan Science and Technology Agency, Japan [retrieved on Nov. 28] Retrieved from: JST Document Retrieval System for Academic and Medical Fields, Japan reference No. 07A1067170.

* cited by examiner

*Primary Examiner* — Michael G Hartley
*Assistant Examiner* — Lance Rider
(74) *Attorney, Agent, or Firm* — Wenderoth, Lind & Ponack, L.L.P.

(57) ABSTRACT

This invention provides organic-inorganic hybrid particles containing as the essential components a block copolymer comprising an uncharged hydrophilic polymer chain segment and a polymer chain segment containing a repeated structural unit having a carboxylate ion group at its side chain; calcium ion ($Ca^{2+}$), phosphate ion ($PO_4^{3-}$) or carbonate ion ($CO_3^{2-}$), or a mixture of these anions; and a contrast agent. The particles provide, in particular, carriers for stably delivering an MRI contrast agent to a target site.

8 Claims, 10 Drawing Sheets

(a)

(b)

(a)

(b)

(c)

(d)

(a)

(b)

(c)

(d)

ORGANIC-INORGANIC HYBRID PARTICLES CONTAINING CONTRAST AGENT

This application is a U.S. national stage of International Application No. PCT/JP2007/067556 filed Sep. 4, 2007.

TECHNICAL FIELD

This invention relates to organic-inorganic hybrid particles, more specifically, to organic-inorganic hybrid particles containing contrast agent.

BACKGROUND ART

The importance of early detection of cancer for improving the patients' quality of life (QOL) has been pointed out in recent years. For example, according to a graph on 5-year survival rate of stomach cancer cases, the survival rate of patients whose stomach cancer is detected in the initial stage (first stage) is 90%. By contrast, the survival rate of the end stage (fourth stage) stomach cancer patients is less than 10%. This demonstrates the high importance of early diagnosis of cancer in patients for the current therapy. Also because of frequent lack of subjective symptom of primary cancer, it is necessary to give cancer diagnosis to quite healthy people, in order to ensure the early detection. For this purpose, development of non-invasive and safe method of the diagnosis is desired.

From the viewpoint of non-invasiveness and safety, utilization of MRI (magnetic resonance imaging) appears recommendable, as it uses magnetic field or radio waves and is free of fear of exposure to radiation. However, the present state of art is still unable to detect primary cancer with MRI. Many and various contrast agents in forms easy of handling are being proposed, with the view to obtain still higher contrast to raise sensitivity of MRI (for example, see the Non-patent References 1, 2 and 3 in the collective listing given later, and so forth). While these contrast agents include actually widely used excellent contrast agents such as Gd-DTPA (gadodiamide), it may worth continual investigations if further improvements are possible.

On the other hand, we have developed a drug delivery system using specific block copolymers and succeeded in offering certain anti-cancer drug with increased tumor tissue-selective accumulation, whose favorable therapeutic effect has been clinically confirmed.

Furthermore, there was a method proposed in the past as a means to introduce DNA into cells, which used a complex formed by making use of the property of calcium phosphate (hydroxyapatite) crystals to bind to DNA, the crystals being formed when an aqueous calcium solution and aqueous phosphoric acid solution were mixed to bring about oversaturated condition. A part of us discovered that, in the attempt to improve the disadvantage incidental to the method, the calcium phosphate particles could be formed with controlled size, when incubated with the specific block copolymer containing a hydrophilic, nonionic polyethylene glycol (PEG) segment and a polyanionic segment derived from carboxyl group. We furthermore confirmed that the so obtained particles had not only relatively narrow particle size distribution and that their average particle size could be controlled to be less than submicron order (several hundreds nm) where necessary, but also aqueous dispersion systems containing these particles could be stably stored under ambient conditions, without inducing sedimentation. In consequence, we proposed a novel organic-inorganic hybrid particle system which could carry, as the drug, DNA or other bioactive substances and deliver the drug to cancer tissues or cancer cells (see Patent Reference 1).

LIST OF CITED REFERENCES

Patent Reference 1: International Publication 03/018690 Pamphlet (WO 03/018690 A1)
Non-patent Reference 1: Peter Caravan, et al., "Gadolinium (III) Chelates as MRI Contrast Agents: Structure, Dynamics, and Applications", Chem. Rev. 1999, 99, 2293-2352
Non-patent Reference 2: Vincent Jacques, et al., "New Classes of MRI Contrast Agents" Topics in Current Chemistry (Springer-Verlag) Contrast Agents 1, Magnetic Resonance Imaging, Edited by Werner Krause, 2002, 221, 123-164
Non-patent Reference 3: D. D. Schwert, et al., "Non-Gadolinium-Based MRI Contrast Agents" Topics in Current Chemistry (Springer-Verlag), Contrast Agents 1, Magnetic Resonance Imaging, Edited by Werner Krause, 2002, 221, 165-199.

DISCLOSURE OF THE INVENTION

We now discovered that the specific organic-inorganic hybrid particle system as described in above Patent Reference 1 could effectively encapsulate therein specific contrast agent, besides DNA or such polypeptide bioactive substances as TGF-β, tumor necrosis factor, insulin and so on. Furthermore, while so obtained organic-inorganic hybrid particles showed pH-responsive property in aqueous solutions, we discovered, still in addition, that the particles having more rapid pH-responsive properly could be provided by our newly proposed system in which the phosphate ions were replaced with carbonate ions, or with a mixture of carbonate ions and phosphate ions.

Accordingly, this invention provides organic-inorganic hybrid particles containing as the essential components, a block copolymer comprising a structure represented by the general formula (I):

poly(hph)-block-poly(carbo)    (I)

in the above formula, poly(hph) stands for an uncharged hydrophilic polymer chain segment and poly(carbo) stands for a polymer chain segment containing a repeated structural unit having a carboxylate ion group at its side chain, calcium ion ($Ca^{2+}$) and phosphate ion ($PO_4^{3-}$) or carbonate ion ($CO_3^{2-}$), or a mixture of these anions, and a contrast agent.

Furthermore, as the invention of a preferred different embodiment, also provided are organic-inorganic hybrid particles containing as the essential components, a block copolymer comprising the structure represented by the general formula (I)

poly(hph)-block-poly(carbo)    (I)

in which poly(hph) stands for an uncharged polymer chain segment and poly(carbo) stands for a polymer chain segment comprising a repeated structural unit having a carboxylate ion group at its side chain, calcium ion ($Ca^{2+}$) and carbonate ion ($CO_3^{2-}$) or a mixture of carbonate ion and phosphate ion ($PO_4^{3-}$); and use of the particles.

The particles according to this preferred embodiment easily degrade in aqueous solutions of the pH slightly lower than neutral pH. For example, they show holding property in blood flow, stably retaining their particulate form, but in environments at a pH a little lower than the neutral range (for example, in a fixed tumor tissue), they degrade to release encapsulating substances from the particle. Furthermore, such properties possessed by the organic-inorganic hybrid particles containing carbonate ions further exhibit unique effect, particularly when Gd-based chelate encapsulates in the particle is used as the contrast agent. Differently from iron-based particles or contrast agents other than MRI of which presence per se enhances the signals, Gd-based chelate enhances the signals by affecting the surrounding protons (mainly protons of water). In MRI, when pulse waves are applied under strong static magnetic field, relaxation time of the protons of Gd-surrounding water is shortened and the signal intensity increases. Therefore, it is important that the contrast agent is released from the hybrid particles at the signal-generating place and can approach the water in situ.

The organic-inorganic hybrid particles containing carbonate ions exhibit tumor tissues-targetability and also easy degradability in situ. Hence, when the particles encapsulate Gd-based chelate type contrast agent, clear contrast can be enhanced, for example, between the blood flow and the tumor tissues.

According to the present invention, regardless a contrast agent is either additionally carried or absent, substantially spherical particles are offered, and furthermore such particles of controlled average particle size and narrow particle size distribution are offered. The average particle diameter can range from about 5-about 5,000 nm, preferably from about 10-1,000 nm, inter aha, from about 50-about 600 nm.

DETAILED DESCRIPTION OF THE INVENTION

One of the characteristic features of the present invention resides in the use of a block copolymer containing the structure represented by the general formula (I),

poly(hph)-block-poly(carbo)        (I)

in the above formula, poly(hph) stands for an uncharged hydrophilic polymer chain segment, and poly(carbo) stands for a polymer chain segment comprising a repeated structural unit having carboxylate ion group in its side chain, in a system producing calcium phosphate (hydroxyapatite), in particular, calcium carbonate.

"Calcium phosphate" or "calcium carbonate" in the present specification as referred to in the above signify those amorphous fine agglomerates formed through the interaction between the ions constituting them and the block copolymer in an aqueous medium, not their complete crystals. Although not to be theoretically bound, it is understood that the polycarboxylate-containing chain segment of the block copolymer interacts with the calcium ion, phosphate ion or carbonate ion, or the mixture of these anions to form the fine agglomerate, while the uncharged hydrophilic polymer chain segment forms a hydrophilic shell-like layer surrounding the fine agglomerate.

Therefore, any kind of copolymer can be used as the block copolymer so long as it functions as described in the above, can form the intended organic-inorganic hybrid particles and falls within the scope of the definitions given as to the general formula (I), regardless either of the segments is derived from natural substance or synthetic polymer. Whereas, although not in limitative sense, as specific examples of poly(hph), those containing a polymer chain segment derived from a polymer selected from the group consisting of polyethylene glycol (PEG), poly(2-methyl-2-oxazoline), poly(2-ethyl-2-oxazoline), poly(2-isopropyl-2-oxazoline), poly(acrylamide), poly(methacrylamide), poly(vinyl alcohol), poly(hydroxyethyl acrylate) and poly(hydroxyethyl methacrylate) can be named. On the other hand, poly(carbo) can be a polymer chain segment derived from a polymer selected from the group consisting of poly(aspartic acid), poly(glutamic acid), poly(acrylic acid), poly(methacrylic acid), poly(malic acid) and random or block copolymers produced from at least two monomers for making these polymers. Copolymers composed of combination of any of such specific examples of poly(hph) and poly(carbo) are the more specific copolymers useful for the present invention.

While some of these copolymers are commercially available, they can be made by well known methods in the concerned art or modifications thereof. For example, where poly(carbo) is a segment derived from poly(aspartic acid) or poly(glutamic acid), poly(oxazoline) or polyethylene glycol with aminated terminus is used as the initiator for ring-opening polymerization of N-carboxylic anhydride in which the corresponding β- or γ-carboxyl group is protected, thereafter detaching the protective group by hydrolysis (see, for example, "Macromolecules", 1997, 30, 4013-4017). Where poly(carbo) has a segment derived from, for example, poly(methacrylic acid) or poly(acrylic acid), one end of the uncharged segment may be modified with an initiator which supplies a radical to induce polymerization of each monomer. Furthermore, it is also possible to couple the anion segment with uncharged segment, utilizing Michael's addition reaction or the like.

In the poly(carbo), a fixed carboxylate ion can either have a counter ion derived from alkali metal (sodium, potassium or the like) or be in an ester form (e.g., lower alkyl ester having up to six carbon atoms or benzyl ester) depending on the production method of the block copolymer. According to the invention, a residue in the ester of such form may be contained up to about 50%, as long as its presence does not hinder encapsulation or adsorption of the block copolymer into or onto calcium phosphate or calcium carbonate, which however is preferably less than 10%, inter alia, 0%.

The wording used in defining the block copolymer: it "comprises the structure" represented by the formula (I), is intended to signify that the linker between poly(hph) and poly(carbo) and the terminus of the polymer (or poly(carbo)) may contain any optional group or moiety, so long as it meets the object of the present invention. Each of the polymer segments can take a wide variety of binding forms (or via a linker or without a linker) mainly depending on the production method of the copolymer, so long as they achieve the above-described functions. These two segments may be linked by a linker in which 1-20 atoms usually suitably selected from carbon, oxygen, sulfur and nitrogen atoms can be linearly present continuously.

As more specific, preferred copolymers, block copolymers represented by following formulae (II-a), (II-b), (III-a), (III-b) and (IV) can be named, although not limited thereto.

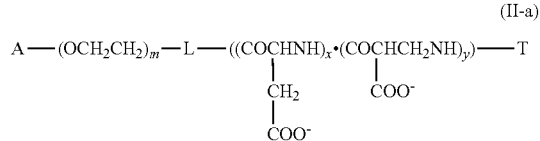
(II-a)

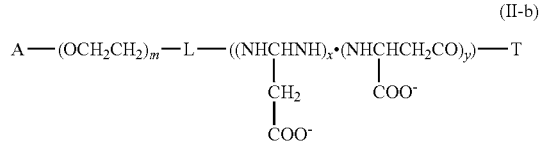
(II-b)

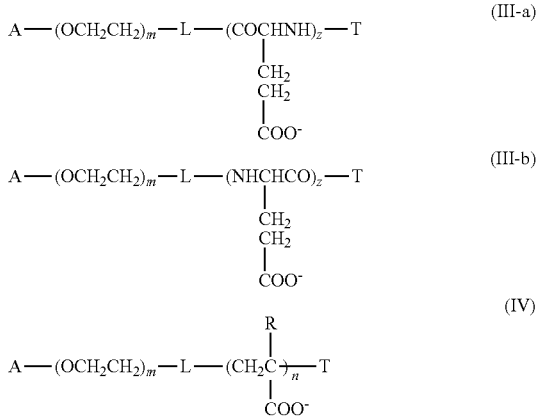

in the above formulae, each symbol has a signification independently of each other, and A stands for hydrogen or a substituted or unsubstituted alkyl having up to 12 carbon atoms, L stands for direct bond or a divalent linker, for example O, NH, CO or X(CH$_2$)pY in which X stands for OCO, OCONH, NHCO, NHCOO, NHCONH, CONH or COO, Y stands for NH or CO, and p is an integer of 1-6, T stands for hydrogen, hydroxyl or —ZR in which Z stands for single bond, CO, O or NH, and R stands for a substituted or unsubstituted hydrocarbon group having up to 12 carbon atoms, m is an integer of 4-2,500, n is an integer of 5-10,000, preferably 10-3,000, inter alia, 10-500, and x+y or z is an integer of 5-1,000, preferably 10-3,000, inter alia, 10-500, wherein up to 50% of the carboxylate ion present can either have a counter ion derived from the alkali metal or form a carboxy ester residue.

Also the dot mark "•" between α-aspartic acid unit and β-aspartic acid unit in the above formulae (II-a) and (II-b) signifies that these units are present at random.

Those definitions of respective groups or moieties in the above formulae more specifically have the following significations. "Alkyl having up to 12 carbon atoms" (which may hereafter be abbreviated as C$_{12}$, this expression being similarly used for other groups containing carbon atoms) include straight chain or branched chain alkyl such as methyl, ethyl, n-propyl, iso-propyl, n-butyl, sec-butyl, n-pentyl, n-hexyl and n- or iso-dodecyl. Substituents on these alkyl groups can be any, so long as they meet the object of the present invention, while those preferred are hydroxyl, carboxyl, a group represented by the formula R$^1$R$^2$CH— (here R$^1$ and R$^2$ each independently stands for C$_{1-10}$ alkyloxy, aryloxy or aryl-C$_{1-3}$ alkyloxy, or may together stand for optionally C$_{1-6}$ alkyl-substituted ethylenedioxy(—O—CH(R')—CH—O—, here R' being hydrogen or C$_{1-6}$ alkyl), a group represented by the formula, R$^{1'}$R$^{2'}$NCH$_2$— (wherein R$^{1'}$ and R$^{2'}$ stand for, independently of each other, organic silyl type amino-protective group, e.g., trialkylsilyl, or R$^{1'''}$ and R$^{2'}$ are atomic groups capable of forming, together with the nitrogen atom to which they bind, a 4- to 7-membered disilaneazacyclo heterocyclic ring). For example, the group of the formula R$^1$R$^2$CH— stands for so called "acetal moiety", and can be readily converted to aldehyde group (OCH—) by mild hydrolysis. On the other hand, the group of the formula R$^{1'}$R$^{2'}$NCH$_2$— can be readily converted to H$_2$N—, for example, in a solution containing tetraalkylammonium fluoride. Therefore, when the block copolymers represented by the general formulae (I), (II-a), (II-b), (III-a), (III-b) or (IV) having such substituent groups are used to form those organic-inorganic hybrid particles (for example, polymeric micelles) of the present invention and thereafter the substituents, which are normally present on the shells or surfaces of the particles, are converted to aldehyde or amino groups, thus obtained functional groups can be conveniently used to covalently bond the particles therethrough, to polypeptides having specific binding ability, for example, sugar residue such as lactose, antibody and the like. It is also possible to impart to the particles still enhanced target directivity. Methods for obtaining polyethylene segments having such substituents are known. For example, WO 96/33233 (or corresponding U.S. Pat. No. 5,925,720) can be referred to, for preparing one having R$^1$R$^2$CH— group as the substituent.

In the so obtained block copolymers, T in the above formulae (II-b), (III-a) and (III-b), or end groups corresponding thereto can be normally hydrogen or hydroxyl. Into these end groups, —ZR group can be introduced by the means known per se, examples of R including hydrocarbon groups such as —CH$_3$, —CH$_2$CH$_3$, —CH═CH$_2$, —C(CH$_3$)═CH$_2$, —CH$_2$

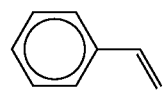

and so on, although not limited thereto.

Introduction of such groups can be done, again following the method described in U.S. Pat. No. 5,925,720.

Contrast agent which is contained in the organic-inorganic hybrid particles according to the invention can be adhered onto the fine agglomerates' surface or, preferably, are whole encapsulated.

The contrast agent can be of any kind, so long as it meets the object of the present invention. Preferred examples are those named in the Non-patent Reference 1, Non-patent Reference 2 or Non-patent Reference 3 (being cited herein, the whole contents of these References serve as a part of this specification). As specific examples, it can be a metal selected from the group consisting of gadolinium (Gd), europium (Eu), manganese (Mn), iron (Fe) and copper (Cu), although not limited thereto. These metals furthermore can be in the form of a metal chelate with polydentate ligands which can be selected from aminocarboxylic acid or phosphoric acid system, porphyrin system and deferoxamine B system polydentate ligands. Although not limited thereto, examples of aminocarboxylic acid or phosphoric acid system polydentate ligands include ethylenediamine tetraacetic acid, diethylenetriaminepentaacetic acid, triethylenetetraminehexaacetic acid, ethylene glycol tetraminetetraacetic acid, tetraazacyclododecanetetraacetic acid, tetraazacyclododecanetriacetic acid, tetraazacyclododecane-tetraphosphoric acid and so on; examples of porphyrin system polydentate ligand include porphyrin and so on; and examples of deferoxamine system polydentate ligand include deferoxamine B and so on.

According to the present invention, also provided are aqueous dispersion compositions for forming organic-inorganic hybrid particles containing the contrast agent, which comprise above-described block copolymer, and calcium ion and phosphate ion, carbonate ion or a mixture of these ions (in particular, carbonate ion), as the essential components. The "aqueous dispersion composition" referred to herein or later-describing term, "aqueous dispersion" signify solutions, dispersions or suspensions comprising a solvent system in which water serves as the chief solvent and which may optionally contain a minor amount of water-miscible organic solvent (e.g., methanol, ethanol, acetone and the like) within a range not affected to accomplishment of the object of the present invention. These liquids preferably contain a buffer which is capable of adjusting pH to 6.0-8.0. The calcium ions and phosphate ions or carbonate ions contained in these liquids can be derived from respectively corresponding water-soluble salts. Typically, the former is derived from calcium chloride and the latter, from disodium hydrogenphosphate or sodium hydrogencarbonate.

The ratio between the calcium ion content and phosphate ion or carbonate ion content is considerably important for the present invention. It is normally necessary that the calcium ions should be present in an amount exceeding the equivalent amount required for the two kinds of ions to react to form calcium phosphate or calcium carbonate. More specifically, the ratio of $Ca^{2+}$ to $PO_4^{3-}$ or $CO_3^{2-}$ can range from 1-1000:1 in terms of molar concentration. When calcium ions and phosphate ions or carbonate ions are present at a ratio falling within the above range, these ions and the block copolymer can conveniently interact.

Also in the aqueous composition, $Ca^{2+}$ can be present at 10 mM-1,000 mM, although not limited thereto, and $PO_4^{3-}$ or $CO_3^{2-}$, at 0.4 mM-10 mM, although not limited thereto. Such ratios are suitable for having the aqueous composition include a contrast agent and providing an aqueous dispersion according to the present invention which comprises the organic-inorganic hybrid particles carrying or encapsulating such a contrast agent.

On the other hand, the block copolymer can be present in the aqueous composition at a concentration of 10 μg/ml-1,000 although not limited thereto. These $Ca^{2+}$ and $PO_4^{3-}$ or $CO_3^{2-}$ concentration values as above and that of the block copolymer in the aqueous composition as above are convenient for maintaining the organic-inorganic hybrid particles (not containing any contrast agent) as formed in the aqueous composition or the organic-inorganic hybrid particles (containing a contrast agent) in the aqueous dispersion, in generally stably dispersed state in an aqueous liquid. Aqueous compositions or aqueous dispersions meeting the object of the present invention, however, can be offered also when these components are used at concentration values exceeding the above-specified ranges. Such aqueous dispersions can be converted to a dry form by per se accepted means, for example, lyophilization. The composition in such dry form can be reconstituted into the stable aqueous dispersion with an aqueous medium, or may be formulated into preparations of different form retaining the dry condition, using other binder or the like where necessary.

The aqueous dispersions according to the present invention which have been partially referred to in the foregoing, can be prepared by having a contrast agent concurrently present in the above-described aqueous composition. More specifically, it can be prepared by (A) preparing a first aqueous solution containing a contrast agent, calcium ion and, where necessary, a buffer, (B) separately preparing a second aqueous solution containing a block copolymer comprising a structure represented by the general formula (I),

poly(hph)-block-poly(carbo)    (I)

in which poly(hph) and poly(carbo) have the previously given significations,
carbonate ion or phosphate ion, and where necessary, a buffer, and (C) mixing the first aqueous solution and the second aqueous solution under the conditions satisfactory for producing calcium carbonate or calcium phosphate, although the method is not limited thereto. It is also possible for the second aqueous solution to contain a salt such as sodium chloride or the like, and the buffer, if used, is recommendably so selected as to enable to adjust pH of the eventual dispersion to 6.0-8.0.

Although not limited to such a preparation method as above, the particles according to the present invention, which are contained in the aqueous dispersion, are contrast agent-carrying particles formed of above-described block copolymer, calcium ion and carbonate ion or phosphate ion, and the contrast agent. Their average particle diameter can be readily controlled within a range of 5-2000 nm, as determined by dynamic light-scattering measurement of the dispersion. According to the above preparation method of the present invention, for example by selecting the block copolymer concentration, an aqueous dispersion of highly uniform particles having an optional diameter within a range of 50-600 nm and a degree of polydispersion not more than 0.1 can be provided. Needless to say, where necessary, particles of the diameter exceeding 600 nm and in the order of several μm can be provided by extending the preparation time. These aqueous dispersions can be stored for a period ranging from several days to a month under ambient conditions (e.g., room temperature and so on) substantially free of precipitation or phase separation, which makes it possible to use them as injectable compositions either as they are or after removing therefrom excessive ionic low molecular weight compound or the like by dialysis or ultrafiltration.

Although not in any limitative sense, where the organic-inorganic hybrid particles following the present invention contain the following components, the components' ratios by weight can be as follows: block copolymer:$CaCO_3$:Gd-PTDA=0.2-1.6:0.3:0.05-0.1, or block copolymer:$Ca_3(PO_4)_2$:Gd-DTPA=0.2-1.6:0.4-0.65:0.05-0.1.

The organic-inorganic hybrid particles following the present invention can be stably maintained or preserved in a biological fluid at around neutral pH, for example, blood. The particles furthermore exhibit tumor tissue directivity. In particular, the hybrid particles containing carbonate ions or a mixture of carbonate ions and phosphate ions as inorganic ions exhibit pH sensitivity such that they readily degrade in an environment of a pH slightly lower than neutrality. Accordingly, it can be understood that the particles would readily degrade in tumor tissues.

BEST MODE FOR WORKING THE INVENTION

Hereinafter the present invention is explained more concretely, referring to specific examples, it being not intended to limit the invention to these examples.

Example 1

Diameter Control of Composite Particles of Gd Chelate and Calcium Phosphate

This experiment demonstrates the effectiveness of the specific block copolymer for preventing formation of calcium phosphate (abbreviated as CaP) precipitate, or for forming the particles with their diameters controlled to not more than fixed value.

<Experiment Method>
(1) The following aqueous solutions were prepared.
Solution A: 250 mM $Ca^{2+}$ (derived from $CaCl_2$)
1 mM Tris-HCl Buffer (pH 7.6)
PEG-block-poly(methacrylic acid) (abbreviated as PEG-PMA)
400-3200 µg/ml
Solution B: 6 mM $PO_4^{3-}$ (derived from $Na_2HPO_4$)
50 mM HEPES Buffer (pH 6.6 or 7.1)
140 mM NaCl
1 mM gadolinium-diethylenetriaminepentaacetic acid (abbreviated as Gd-DTPA (Magnevist® purchased from Schering).
In the above, PEG-PMA (purchased from Polymer Source) as represented by the following formula,

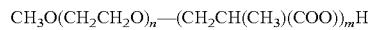

$CH_3O(CH_2CH_2O)_n$—$(CH_2CH(CH_3)(COO))_m H$ in which a block copolymer whose PEG segment had a molecular weight of about 7800 and PMA segment had a molecular weight of about 2000 (abbreviated as 7800-2000), or a block copolymer whose PEG segment had a molecular weight of about 7500 and PMA segment had a molecular weight of about 15500 (abbreviated as 7500-15500) were used in the form of Na salt.
(2) The solution A and solution B were mixed at 37° C. and allowed to incubate at 37° C. for at least 4 hours. Thereafter the particle diameters were evaluated by dynamic light scattering measurement (DLS) of the dispersions.

As the measuring device, Zetasizer Nano ZS of Malvern was used. As the incident light, helium neon laser light of the wavelength 633 nm was used. The measurement was conducted at 37° C. The scattered light in the direction at 173° angle to the incident light was detected, and from the time-dependence of its intensity change, diffusion coefficient of the particles was calculated by cumulant method. Thus obtained diffusion coefficient was converted to particle diameter by the following Stokes-Einstein's equation:

$R=kT/(6\pi\eta D)$ in which R=particle radius, k=Boltzmann's coefficient, T=temperature, η=viscosity coefficient, D=diffusion coefficient.

Using transmission electronic microscope (TEM), CaP particle image also was photographed. The TEM used was H-7000 of Hitachi, used at an acceleration voltage of 75 kV.

Figure 1:
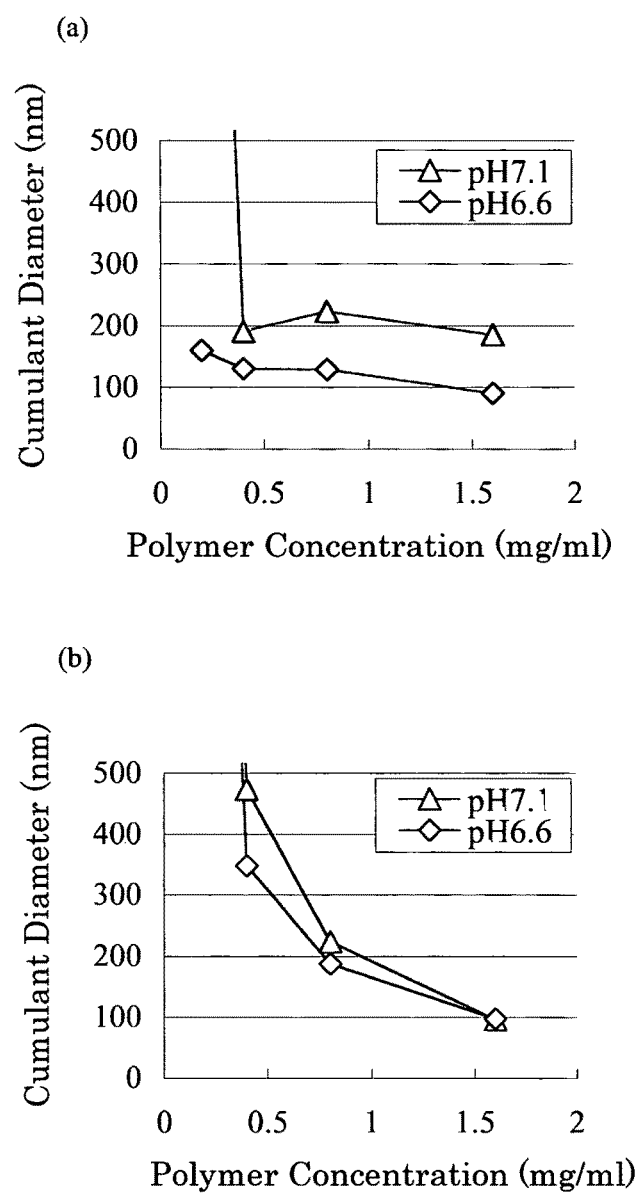
FIG. 1 are the graphs showing the results of measuring diameters of CaP particles by dynamic light scattering method: (a) being a graph of CaP particle diameter versus PEG-PMA (7800-2000) concentration ((Δ) solution B at pH 7.1, (◇) solution B at pH 6.6); and (b) being a graph of CaP particle diameter versus PEG-PMA (7500-15500) concentration ((Δ) solution B at pH 7.1, (◇) solution B at pH 6.6).
Figure 2:
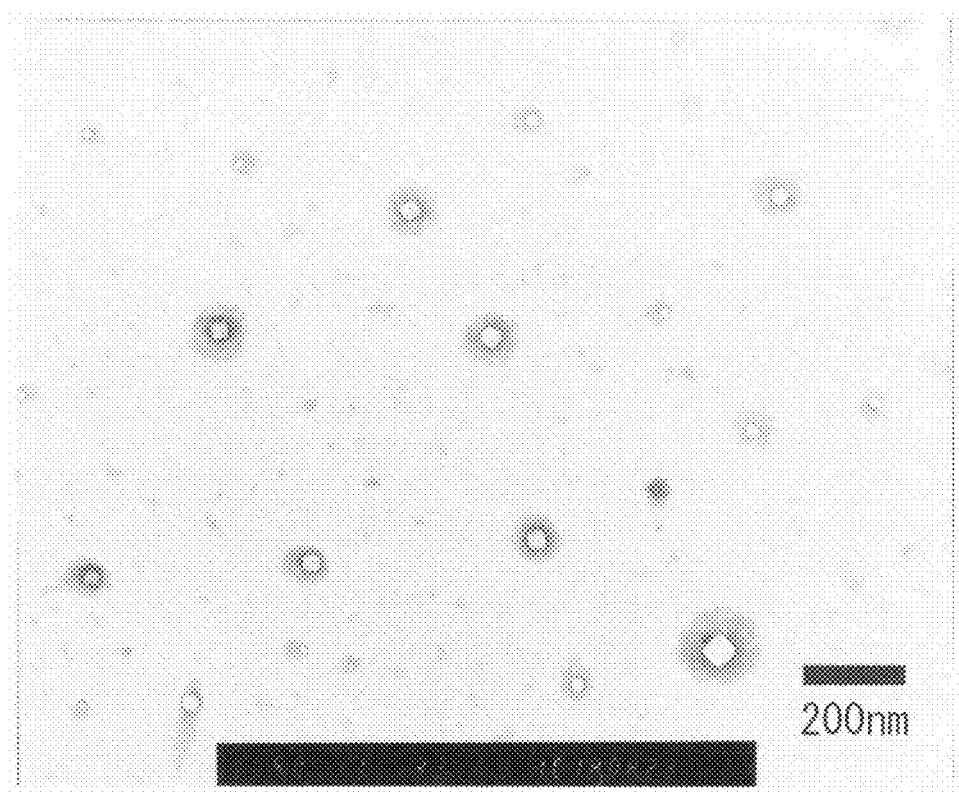
FIG. 2 is a photograph of TEM image of CaP particles. The sample used was the one formed when the solution A contained 3.2 mg/ml PEG-PMA (7500-15500) and the solution B had a pH 7.1. Here the formation of organic-inorganic hybrid micelles having a core of CaP particle and shell of organic molecular layer of the polymer and the like is observed.

<Result>
The influences of pH of the feed, polymer chain length and the polymer concentration on the particle diameter of the formed micelles are shown in FIG. 1. When PEG-PMA (7800-2000) was used, particles diameter control (degree of polydispersion not more than 0.2) was accomplished at more than 0.4 mg/ml of the polymer concentration. The particle diameters were about 100 nm at pH 6.6, and around 200 nm at pH 7.1. When PEG-PMA (7500-15500) was used, the particle diameter control was accomplished at more than 0.8 mg/ml of the polymer concentration. At the polymer concentration of 1.6 mg/ml, the particle diameter was about 100 nm in both cases of pH 6.6 and pH 7.1. As shown in the TEM image (FIG. 2), formation of monodispersed particles of around 100 nm in diameter, having a CaP particle as the core and its shell made of the polymer could be confirmed. The influence of pH on the particle diameter control was distinct with 7800-2000, while it was hardly recognizable with 7500-15500. Also, there was the tendency that the higher the polymer concentration, the easier the particle diameter control, which allows an inference that the influence of PEG on the particle diameter is very strong.

Example 2

Quantitation of Gd-DTPA Introduced into (or Encapsulated in) CaP Particles

Figure 3:
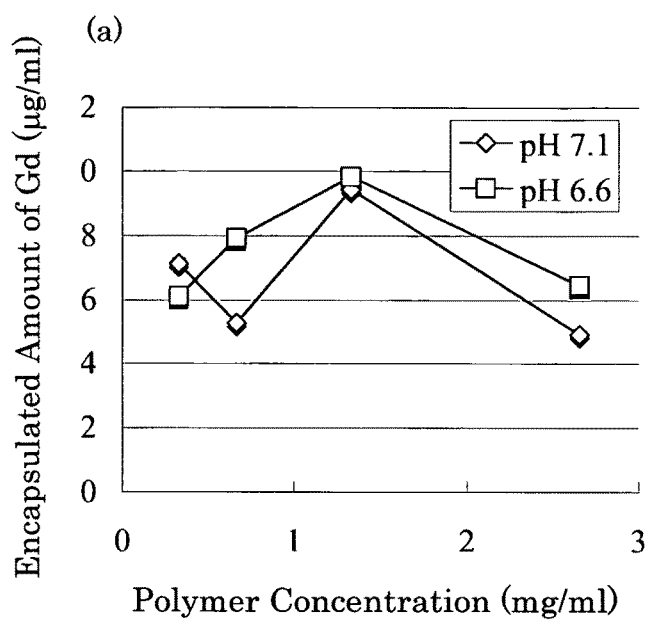
FIG. 3 are the graphs showing the results of determining Gd-DTPA which was encapsulated in the CaP particles, by ICP-MS: (a) being a graph showing the encapsulated amount of Gd in CaP particles versus PEG-PMA (7800-2000) concentration ((Δ) solution B at pH 7.1, (◇) solution B at pH 6.6); and (b) being a graph showing the encapsulated amount of Gd in the CaP particles versus PEG-PMA (7500-15500) concentration ((△) solution B at pH 7.1, (◇) solution B at pH 6.6).
Figure 3:
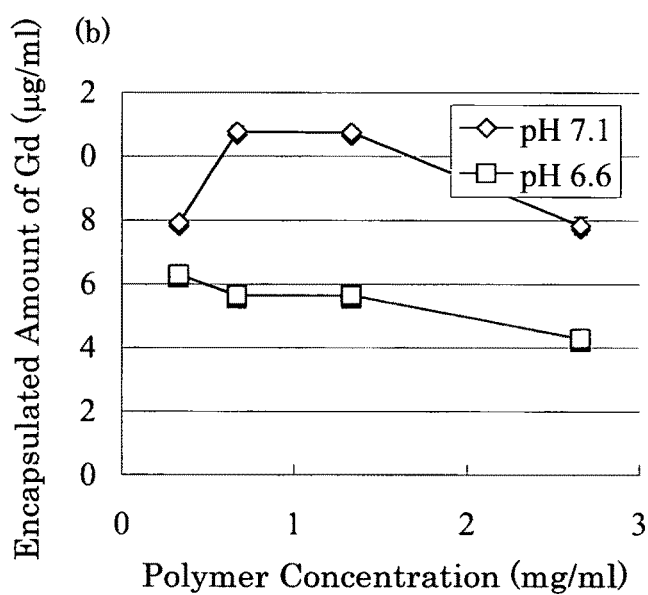

The CaP particles were prepared following above Example 1. One (1) ml of so prepared micelle solution was centrifuged at 15000 G for 30 minutes, and 100 μl of the supernatant was separated. The supernatant was diluted to 50 times with 4.9 ml of 0.1 M HCL solution, and the Gd concentration in the solution was measured with induction-connected plasma mass analyzer (ICP-MS). Whereby concentration of the Gd-DTPA not encapsulated in the calcium phosphate could be known, and the Gd-DTPA encapsulation ratio was calculated and quantitated. The result was as shown in FIG. 3. While the encapsulated amount differed more or less according to the kind and concentration of the polymer, it was basically understood that it amounted to about 10-20% of the fed amount (1 mM Gd-DTPA).

Example 3

Evaluation of Stability of CaP Particles

Figure 4:
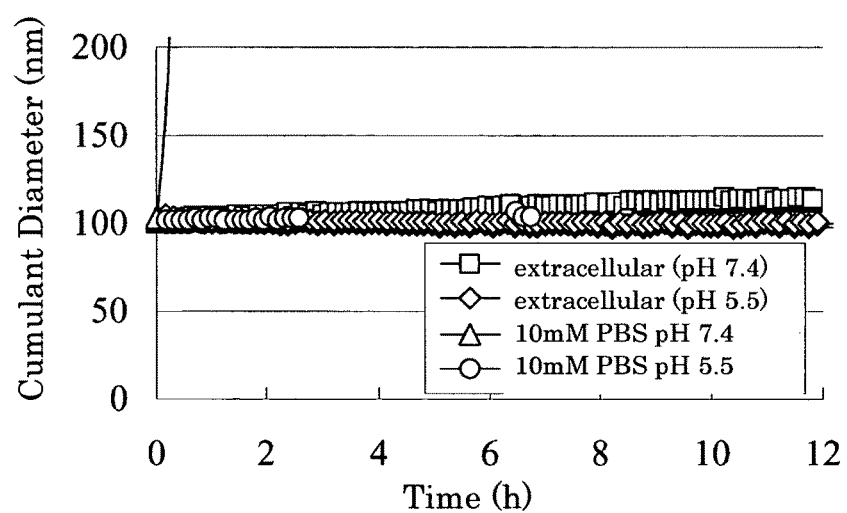
FIG. 4 is a graph showing the particle diameter change with time in CaP particles (PEG-PMA (7500-15500) 3.2 mg/ml, pH 6.6) as measured by dynamic light scattering method, wherein the process of the CaP particles' degradation responsive to the environment can be observed ((□) extracellular solution (pH 7.4), (◇) extracellular solution (pH 5.5), (△) 10 mM PBS (pH 7.4) & 140 mM NaCl, (○) 10 mM PBS (pH 5.5) & 140 mM NaCl).
Figure 5:
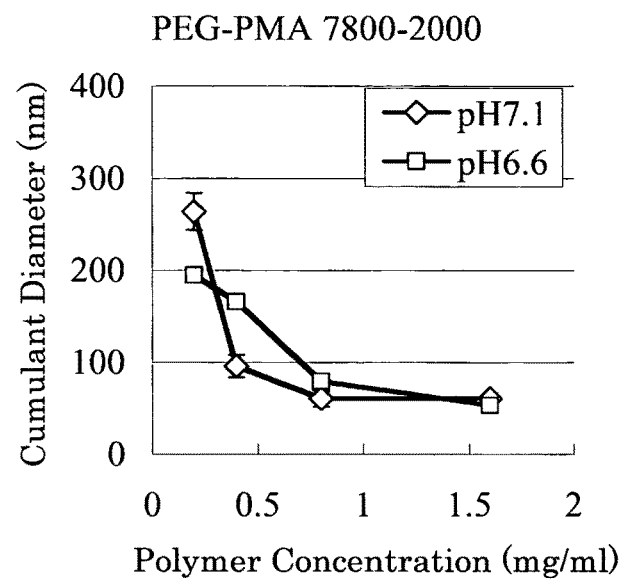
FIG. 5 are the graphs showing the results of particle diameter measurement of $CaCO_3$ particles by dynamic light scattering method, (a) being a graph of $CaCO_3$ particle diameter versus PEG-PMA (7800-2000) concentration ((△) solution B at pH 7.1, (◇) solution B at pH 6.6); and (b) being a graph of $CaCO_3$ particle diameter versus PEG-PMA (7500-15500) concentration ((△) solution B at pH 7.1, (◇) solution B at pH 6.6).
Figure 5:
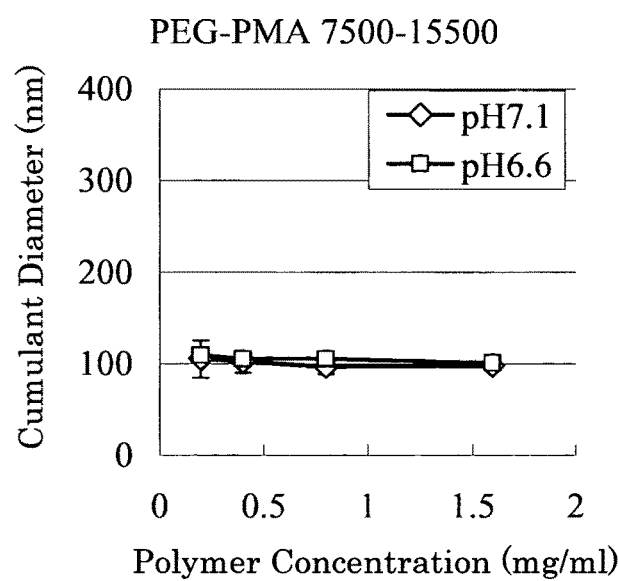

<Experiment Method>
As the sample, the one prepared under the conditions of PEG-PMA (7500-15500) 3.2 mg/ml at pH 6.6, following Example 1, was used. Separately, an extracellular solution (2 mM $CaCl_2$, 1 mM $Na_2HPO_4$, 25 mM Tris, 140 mM NaCl) and 10 mM PBS and 140 mM NaCl solution were prepared, each of which was adjusted in advance to have pH values of 7.4 and 5.5. Two-hundred (200) ml of the sample solution was mixed with 800 μl of each of the separately prepared solutions. The particle size change of each sample was measured for 12 hours by dynamic light scattering. Compositions of the separately prepared solutions were as follows:

extracellular pH 7.4: 2 mM $CaCl_2$, 1 mM $Na_2HPO_4$, 25 mM Tris-HCl Buffer (pH 7.4), 140 mM NaCl extracellular pH 5.5: 2 mM $CaCl_2$, 1 mM $Na_2HPO_4$, 25 mM Tris-HCl Buffer (pH 5.5), 140 mM NaCl, 10 mM PBS pH 7.4: 10 mM phosphoric buffer (pH 7.4), 140 mM NaCl, 10 mM PBS pH 5.5: 10 mM phosphoric buffer (pH 5.5), 140 mM NaCl <Results>
The results are shown in FIG. 4. Stability of the CaP particles markedly varies depending on the phosphoric acid concentration. For example, when the phosphoric acid concentration was increased to 10 mM at pH 7.4, the particles at once agglomerated. Whereas, at pH 5.5 minor elution of calcium phosphate was observed, but with less pH responsivity.

Example 4

Diameter Control of Gd Chelate-Calcium Carbonate Composite Particles

Figure 8:
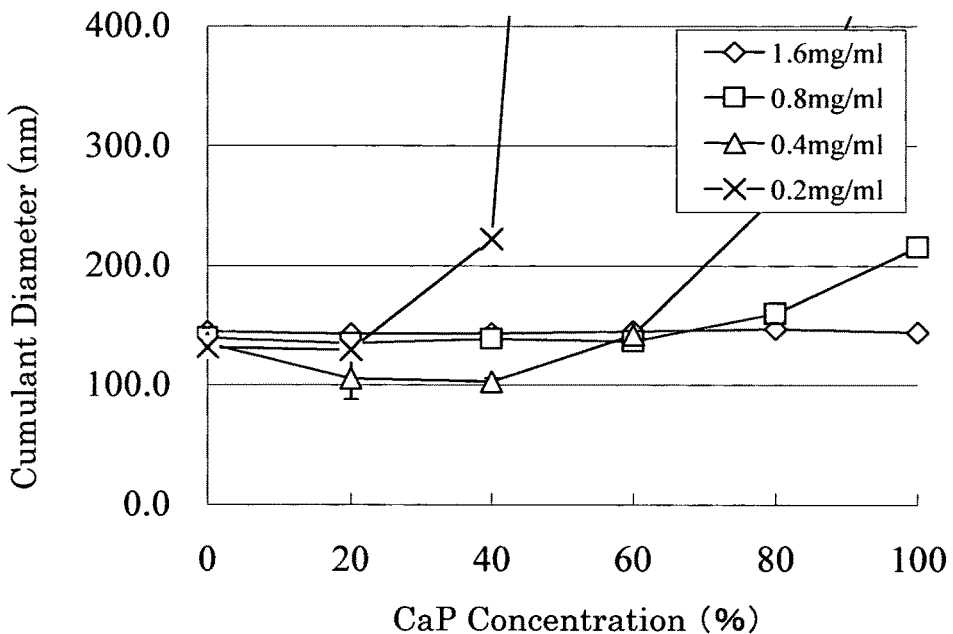
FIG. 8 are the graphs showing the results of diameter measurement of CaP & $CaCO_3$ hybrid particles (($Ca^{2+}$)=250 mM) by dynamic light scattering method: (a) being a graph showing the CaP & $CaCO_3$ hybrid particle diameter versus PEG-PMA (7500-15500) concentration and CaP:$CaCO_3$ ratio; (b) being a graph showing the CaP & $CaCO_3$ hybrid particle diameter versus PEG-PAsp (12-38) concentration and Cap:$CaCO_3$ ratio; (c) being a graph showing CaP & $CaCO_3$ hybrid particle diameter versus PEG-PAsp (12-87) concentration and Cap:$CaCO_3$ ratio, and (d) being a graph showing CaP & $CaCO_3$ hybrid particle diameter versus PEG-PAsp (12-38) concentration and CaP:$CaCO_3$ ratio ((◇) 1.6 mg/ml, (□) 0.8 mg/ml, (△) 0.4 mg/ml, (x) 0.2 mg/ml).
Figure 8:
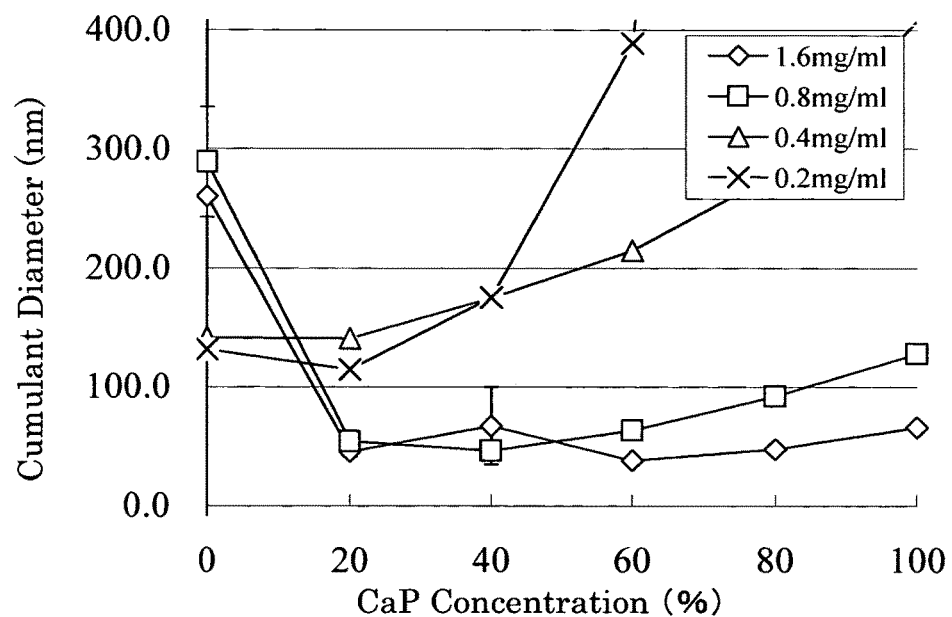
Figure 8:
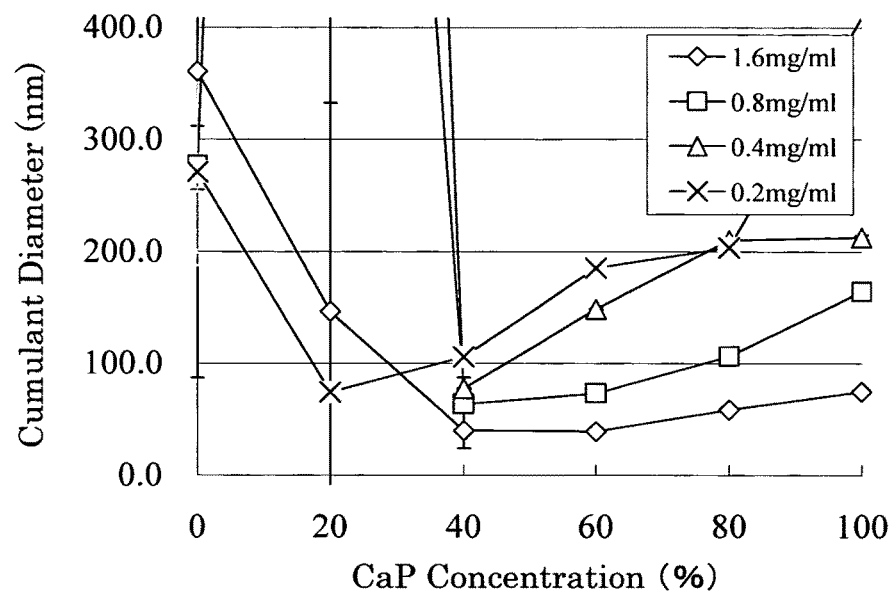
Figure 8:
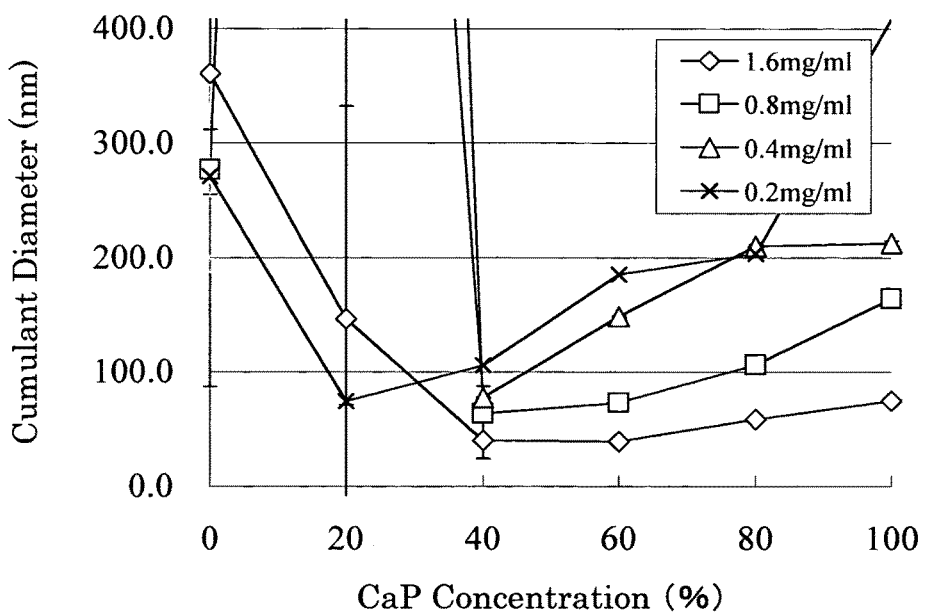

This experiment demonstrates the effectiveness of specific block copolymers for preventing formation of calcium carbonate (abbreviated as $CaCO_3$) precipitate or for producing composite particles having controlled diameters not exceeding a certain fixed value.
<Experiment Method>
(1) The following aqueous solutions were prepared:
Solution A: 250 mM $Ca^{2+}$ (derived from $CaCl_2$)
1 mM Tris-HCl buffer (pH 7.6)
PEG-PMA 400-3200 μg/ml
Solution B: 6 mM $CO_3^{2-}$ (derived from $NaHCO_3$)
50 mM HEPES buffer (pH 6.6 or 7.1)
140 mM NaCl
1 mM Gd-DTPA
As the above PEG-PMA, those of 7800-2000 and 7500-15500 were used in Na salt form.
(2) The solution A and solution B were mixed at 37° C. and allowed to incubate at 37° C. for at least 24 hours. Thereafter the particle diameters were evaluated by dynamic light scattering measurement (DLS) of the dispersions, similarly to Example 1.
<Result>
The influences of pH of the feed, polymer chain length and the polymer concentration on the formed micelle's particle diameter are shown in FIG. 8. Where the PEG-PMA (7800-2000) was used, it was found that particle diameter control was hardly achieved, because the degree of polydispersion was not less than 0.2, although at the first sight it differed depending on the polymer concentration or pH. When PEG-PMA (7500-15500) was used, the partical diameter was well controlled, irrelevantly to the polymer concentration or pH, the particle diameter being about 100 nm and the degree of polydispersion was not more than 0.1. From the result it was understood that the length of anionic segment significantly affects calcium carbonate particle diameter control. It was also confirmed that the particle diameter control was not at all affected by the Gd-DTPA concentration in the feed.

Example 5

Quantitation of Gd-DTPA Introduced into (or Encapsulated in) $CaCO_3$ Particles

Figure 6:
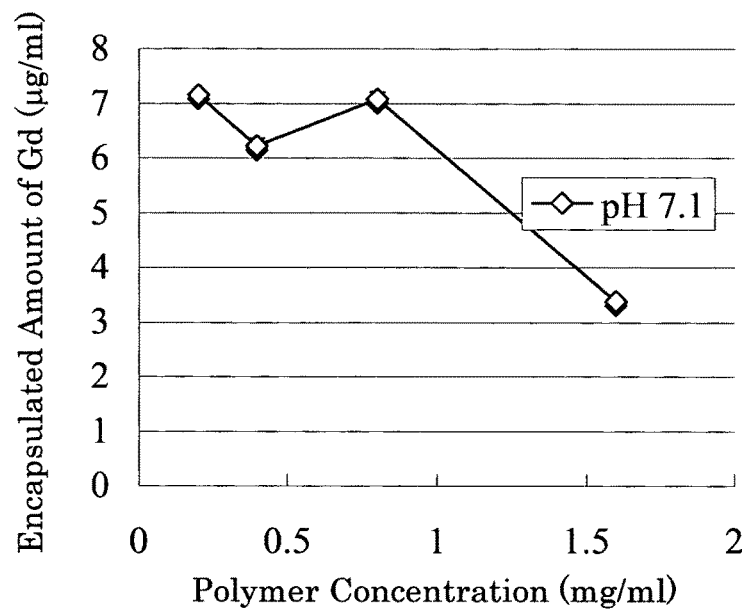
FIG. 6 is a graph showing the result of determining Gd-DTPA which was encapsulated in $CaCO_3$ particles by ICP-MS: a graph showing the encapsulated amount of Gd in $CaCO_3$ particles versus PEG-PMA (7500-15500) concentration ((◇) solution B at pH 7.1).

The encapsulated amount of Gd-DTPA in $CaCO_3$ particles prepared following Example 1 was determined in the manner similar to Example 2. The result was as shown in FIG. 6. The encapsulated amount was approximately the same to that of the CaP particles as prepared at pH 7.1.

Example 6

Evaluation of Stability of $CaCO_3$ Particles

With the view to examine whether the particles would degrade responsive to pH, this stability evaluation was conducted at pH 5.5 and pH 7.4.
<Experiment Method>
As the sample, the one prepared under the conditions of PEG-PMA (7500-15500) 3.2 mg/ml at pH 6.6, following Example 1, was used. Separately, an extracellular solution (2 mM $CaCl_2$, 1 mM $Na_2HPO_4$, 25 mM Tris, 140 mM NaCl) and 10 mM PBS and 140 mM NaCl solution were prepared, each of which was adjusted in advance to have pH values of 7.4 and 5.5. Two-hundred (200) ml of the sample solution was mixed with 800 µl of each of the separately prepared solutions. The particle size change of each sample was measured for 12 hours by dynamic light scattering. Compositions of the separately prepared solutions were as follows:

10 mM PBS pH 7.4: 10 mM phosphoric buffer (pH 7.4), 140 mM NaCl
10 mM PBS pH 5.5: 10 mM phosphoric buffer (pH 5.5), 140 mM NaCl
<Result>

Figure 7:
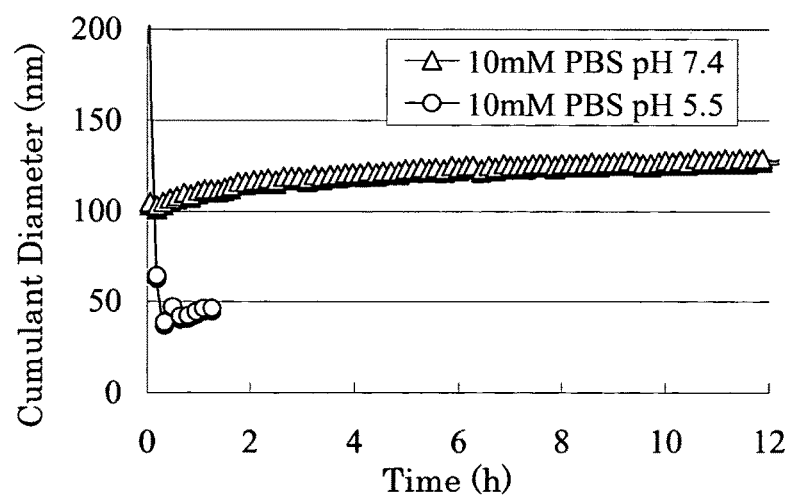
FIG. 7 is a graph showing the particle diameter change with time in $CaCO_3$ particles (PEG-PMA (7500-15500) 3.2 mg/ml, pH 7.1) as measured by dynamic light scattering method, wherein the process of the $CaCO_3$ particles' degradation responsive to the environment can be observed ((△) 10 mM PBS (pH 7.4) & 140 mM NaCl, (○) 10 mM PBS (pH 5.5) & 140 mM NaCl).

The result was as shown in FIG. 7. At pH 7.4, it was confirmed that the particles could be stably present in the solution basically for at least 12 hours, although minor increases in particle diameters or light scattering intensity were observed. On the other hand, it can be understood that the particle diameters and light scattering intensity at once extremely decreased at pH 5.5. This allows an inference that the $CaCO_3$ particles were unstable at pH 5.5 and at once degraded.

Example 7

Diameter Control of Gd Complex and CaP & $CaCO_3$ Hybridized Composite Particles (1)

In Examples 1 and 4, diameter control of composite particles by varying the copolymer concentration or polymer chain length was shown. In this Example, it is shown that the particle diameter can further be adjusted by varying copolymer concentration or kind of the polymer, or the ratio of phosphoric acid to carbonic acid.
<Experiment Method>
(1) The following aqueous solutions were prepared:
Solution A: 250 mM $Ca^{2+}$ (derived from $CaCl_2$)
1 mM Tris-HCl buffer (pH 7.6)
PEG-PMA (7500-15500) or PEG-Polyaspartic acid (abbreviated as PEG-PAsp) 400-3200 µg/ml
Solution B: 6 mM $PO_4^{3-}$ (derived from $Na_2HPO_4$)
50 mM HEPES buffer (pH 7.1)
140 mM NaCl
1 mM Gd-DTPA
Solution C: 6 mM $CO_3^{2-}$ (derived from $NaHCO_3$)
50 mM HEPES buffer (pH 7.1)
140 mM NaCl
1 mM Gd-DTPA
In the above, PEG-PAsp's represented by the following formula,

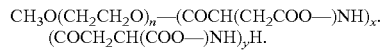
$CH_3O(CH_2CH_2O)_n$—$(COCH(CH_2COO—)NH)_x$-$(COCH_2CH(COO—)NH)_y$H.

in which the molecular weight of the PEG segment was about 12,000 and the degree of polymerization (x+y) of the PAsp segment was 87 and 38, respectively, (abbreviated as 12-87 and 12-38, respectively) were prepared and used.

Above solutions B and C were mixed at the ratios of 100:0, 80:20, 60:40, 40:60, 20:80 and 0:100, respectively, to make solutions D. (2) The solution A and each solution D were mixed at 37° C., allowed to incubate at 37° C. for at least 24 hours. Thereafter particle diameter were evaluated by dynamic light-scattering measurement (DLS) of the dispersions similarly to Example 1.
<Result>

The influences of the phosphate:carbonate ratio in the feed, kind of polymer and the polymer concentration on diameter of the formed micelles were as shown in FIG. 8. Where PEG-PMA (7500-15500) was used and the polymer concentration was 3.2 mg/ml, the particle diameters did not vary irrelevantly to the ratio between the phosphate and carbonate. Because the degree of polydispersion was not more than 0.2, it was found that the particle diameter control could be done at this concentration. It was also found, furthermore, when the phosphate to carbonate ratio was biased to phosphate side, a tendency was developed that the lower the polymer concentration, the easier the agglomeration. On the other hand, where PEG-PAsp (12-87) was used, the polymer concentration range enabling the particle diameter control was found to be narrower than that with PEG-PMA (7500-15500). When $CaCO_3$ was 100%, the concentration range enabling the particle diameter control lied at low polymer concentration, but as the ratio of phosphate rose, the particle size controllable range was enlarged and shifted toward high polymer concentration, showing a tendency that the particle diameters decreased under high polymer concentration and high phosphoric acid concentration. Where PEG-PAsp (12-38) was used, CaP particle diameters could be controlled over a wide concentration range, but no $CaCO_3$ particle was formed. When CaP—$CaCO_3$ hybrid type was used, the particle diameter control over a wide concentration range became possible under the phosphate ratio of 40-100%.

Example 8

Diameter Control of Gd Complex and CaP & $CaCO_3$ Hybridized Composite Particles (2)

In Example 7, diameter control of the composite particles by varying the copolymer concentration, kind of polymer or the ratio between phosphoric acid and carbonic acid was shown. In this example, it is shown that the particle diameter can be further controlled at a Ca concentration ($[Ca^{2+}]$=25 mM) which is different from that ($[Ca^{2+}]$=250 mM) used in Example 7.
<Experiment Method>
(1) The following aqueous solutions were prepared.
Solution A: 25 mM $Ca^{2+}$ (derived from $CaCl_2$)
1 mM Tris-HCl buffer (pH 7.6)
PEG-PMA (7800-2000, 7500-15500) or
PEG-PAsp (12-87, 12-38) 400-3200 µg/ml
Solution B: 6 mM $PO_4^{3-}$ (derived from $Na_2HPO_4$)
50 mM HEPES buffer (pH 7.1)
140 mM NaCl
1 mM Gd-DTPA
Solution C: 6 mM $CO_3^{2-}$ derived from $NaHCO_3$)
50 mM HEPES buffer (pH 7.1)
140 mM NaCl
1 mM Gd-DTPA.
Above solutions B and C were mixed at the ratios of 100:0, 80:20, 60:40, 40:60, 20:80 and 0:100, respectively, to make solutions D. (2) The solution A and each solution D were mixed at 37° C., allowed to incubate at 37° C. for at least 24 hours. Thereafter particle diameter were evaluated by dynamic light-scattering measurement (DLS) of the dispersions similarly to Example 1.
<Result>

Figure 9:
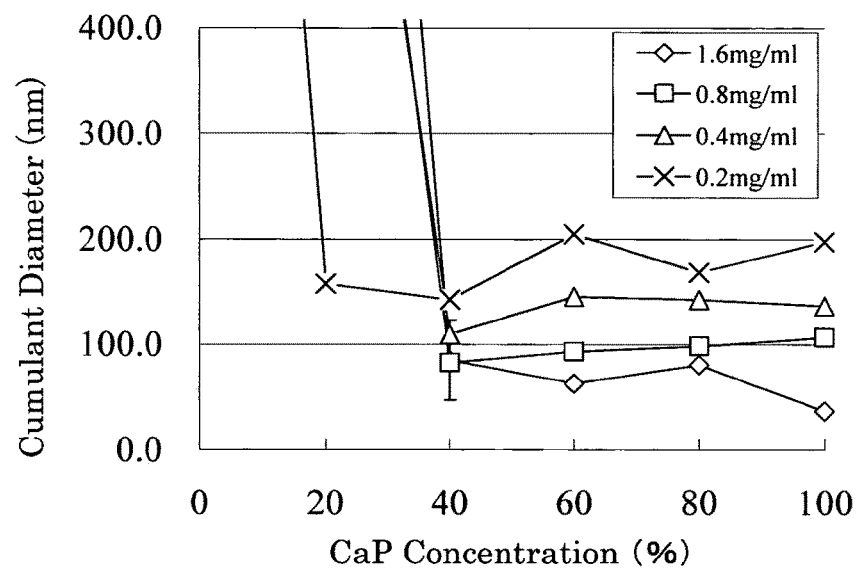
FIG. 9 are the graphs showing the results of diameter measurement of CaP & $CaCO_3$ hybrid particles (($Ca^{2+}$)=25 mM) by dynamic light scattering method: (a) being a graph showing the CaP & $CaCO_3$ hybrid particle diameter versus PEG-PMA (7800-2000) concentration and CaP:$CaCO_3$ ratio; (b) being a graph showing the CaP & $CaCO_3$ hybrid particle diameter versus PEG-PMA (7500-15500) concentration and CaP:$CaCO_3$ ratio; (c) being a graph showing CaP & $CaCO_3$ hybrid particle diameter versus PEG-PAsp (12-38) concentration and CaP:$CaCO_3$ ratio, and (d) being a graph showing CaP & $CaCO_3$ hybrid particle diameter versus PEG-PAsp (12-87) concentration and CaP:$CaCO_3$ ratio ((◇) 1.6 mg/ml, (□) 0.8 mg/ml, (△) 0.4 mg/ml, (x) 0.2 mg/ml).
Figure 9:
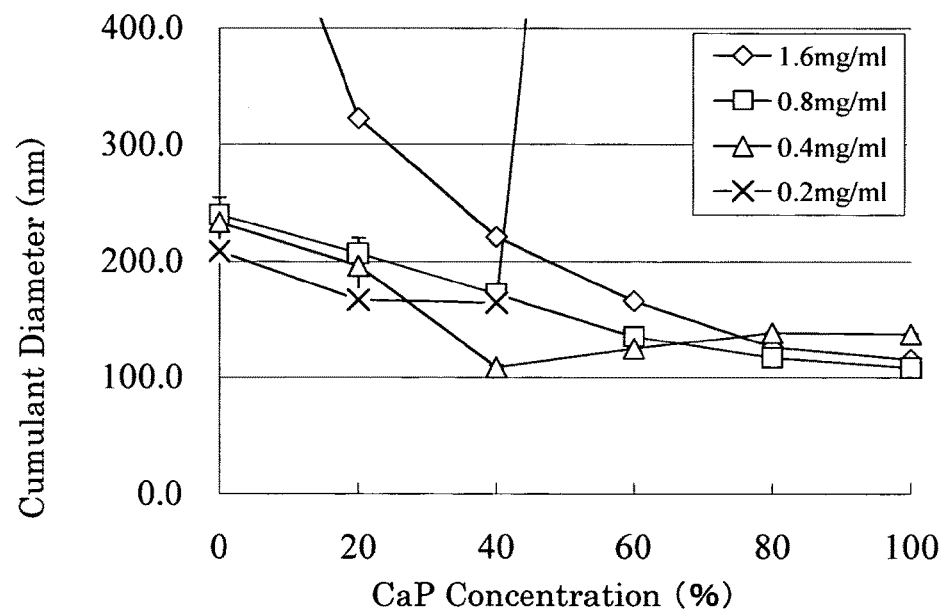
Figure 9:
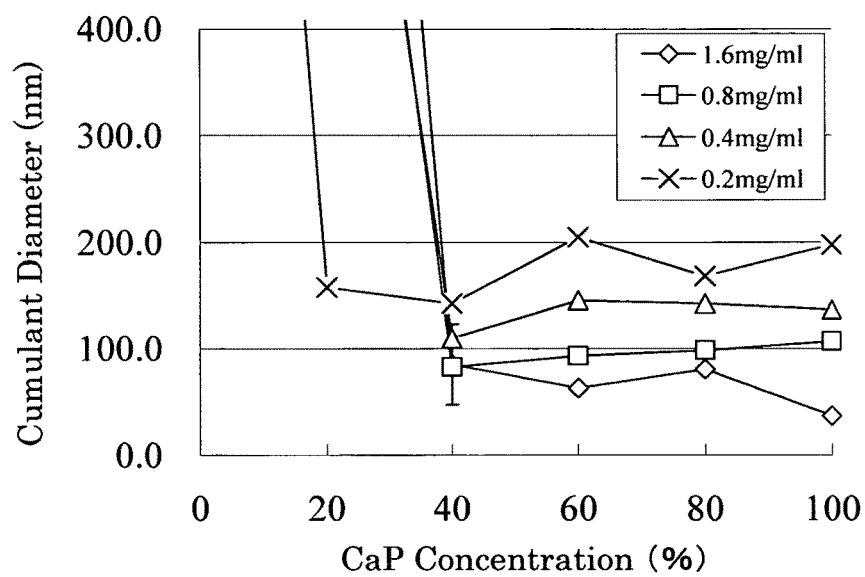
Figure 9:
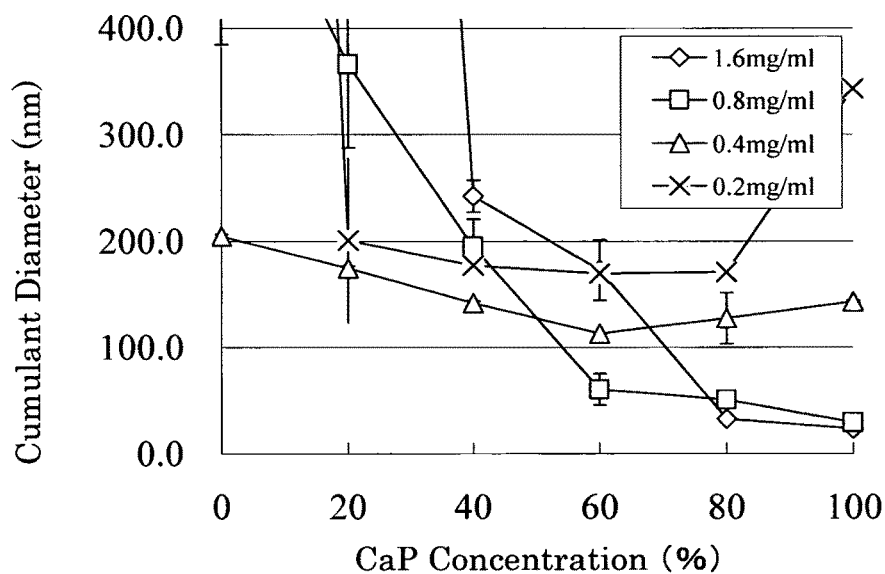

The influences of the phosphate:carbonate ratio in the feed, kind of polymer, and the polymer concentration on diameter of the formed micelles was as shown in FIG. 9. When PEG-PMA (7800-2000) was used, $CaCO_3$ scarcely formed particles, but it was found that the particles were formed over a wide concentration range when 20% or more of the phosphate was used. When PEG-PMA (7500-15500) was used, it was confirmed that $CaCO_3$ particles were formed only under a certain limited polymer concentration range, presumably due to the lowered Ca concentration. It was also observed that the particles were more easily formed with increased ratio of the phosphate, accompanied by shifting of the polymer concentration range to higher side. When PEG-PAsp (12-87) was used, the polymer concentration range enabling the particle diameter control was found to be narrowed. At the polymer concentration of 0.4 mg/ml, however, the particle formation took place irrelevantly to the ratio of phosphate. In case PEG-PAsp (12-38) was used, particle diameter control was possible with CaP particles over a broad concentration range, but no $CaCO_3$ particle could be formed. Where CaP—$CaCO_3$ hybrid type was adopted, the particle diameter control became possible over a broad concentration range, when the ratio of phosphate was 40-100%.

PROSPECT OF INDUSTRIAL UTILIZABILITY

This invention provides, in particular, pH-responsive organic-inorganic hybrid particle system capable of carrying a contrast agent. Such a particle system allows free particle size control within a range from nanometer to micrometer order and can impart to the particles target-selectivity and selective-degradability at the target site. Therefore, the system is useful for the medical industry, diagnostic agent makers and so on.

The invention claimed is:
1. An organic-inorganic hybrid particle comprising as essential components,
a block copolymer comprising a structure represented by a formula (I):

poly(hph)-block-poly(carbo)    (I)

wherein
poly(hph) represents a hydrophilic polymer chain segment derived from a water-soluble polymer selected from the group consisting of poly(ethylene glycol), poly(2-methyl-2-oxazoline), poly(2-ethyl-2-oxazoline), poly(2-isopropyl-2-oxazoline), poly(acrylamide), poly(methacrylamide), poly(vinyl alcohol), poly(hydroxyethyl acrylate) and poly(hydroxyethyl methacrylate);
poly(carbo) represents a polymer chain segment containing a recurring structural unit having a carboxylate ion group at its side chain, wherein the polymer chain segment is derived from the group consisting of poly(aspartic acid), poly(glutamic acid), poly(acrylic acid), poly (methacrylic acid), poly(malic acid) and random or block copolymers produced from at least two monomers for making these polymers;
a calcium ion ($Ca^{2+}$);
at least one anion selected from the group consisting of a phosphate ion ($PO_4^{3-}$), a carbonate ion ($CO_3^{2-}$), and a mixture thereof; and
a contrast agent;
wherein the calcium ion and the phosphate ion form amorphous fine agglomerates, and the calcium ion and the carbonate ion form amorphous fine agglomerates, and
the hybrid particle is in the form of an aqueous dispersion in an aqueous medium, and has an average particle diameter within a range of 10 nm to 1000 nm, as measured by dynamic light-scattering of the dispersion, and
wherein the contrast agent is adhered onto a surface of the amorphous fine agglomerates or is wholly encapsulated by the amorphous fine agglomerates and is a metal selected from the group consisting of gadolinium (Gd), europium (Eu), manganese (Mn), iron (Fe) and copper (Cu), and is in the form of a metal chelate with an aminocarboxylic acid or phosphoric acid system polydentate ligand.

2. The hybrid particle of claim 1, wherein poly(hph) is derived from polyethylene glycol, and poly(carbo) is derived from a polymer selected from the group consisting of poly (aspartic acid), poly(glutamic acid), poly(methacrylic acid), poly(acrylic acid) and poly(malic acid).

3. The hybrid particle of claim 1, wherein the block copolymer is selected from the group consisting of the following formulae (II-a), (II-b), (III-a), (III-b) and (IV):

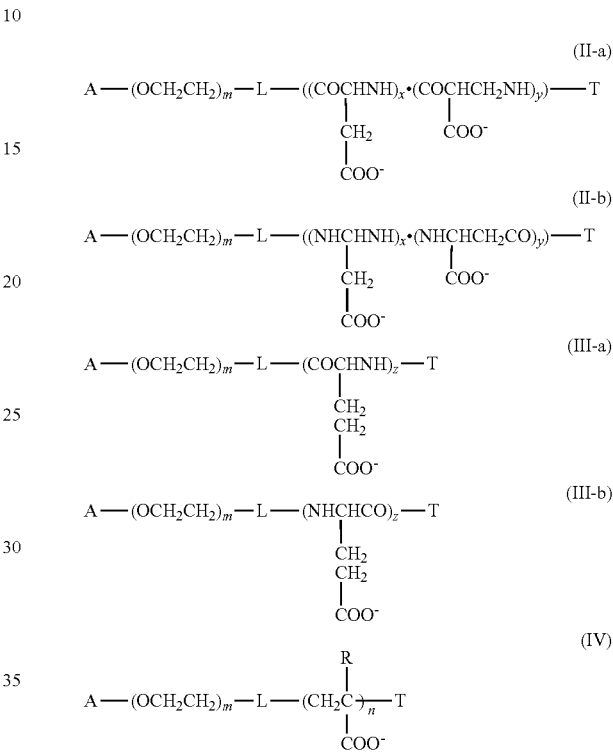

wherein in the above formulae,
each symbol is independently selected,
A represents hydrogen or a substituted or unsubstituted alkyl having up to 12 carbon atoms,
L represents a direct bond or a divalent linker,
T represents hydrogen, hydroxyl or —ZR in which Z represents a single bond, CO, O or NH, and R represents hydrogen or methyl group,
m is an integer of 4-2,500,
n is an integer of 5-10,000,
x+y is an integer of 5-1,000, and
z is an integer of 5-1,000,
wherein up to 50% of the carboxylate ion group present can either have a counter ion derived from an alkali metal or from a carboxy ester residue.

4. The hybrid particle of claim 3, wherein L represents a linker and is selected from the group consisting of O, NH, CO and $X(CH_2)_pY$, where X represents OCO, OCONH, NHCO, NHCOO, NHCONH, CONH or COO, Y represents NH or CO, and p is an integer of 1-6.

5. The hybrid particle of claim 1, wherein the aminocarboxylic acid or phosphoric acid system polydentate ligand is selected from the group consisting of ethylenediaminetetraacetic acid, diethylenetriaminepentaacetic acid, triethylenetetraminehexaacetic acid, ethylene glycol tetraminetetraacetic acid, tetraazacyclododecanetetraacetic acid, tetraazacyclododecanetriacetic acid and tetraazacyclododecanetetraphosphoric acid.

6. The hybrid particle of claim 1, wherein the block copolymer is selected from the group consisting of the following formulae (II-a), (II-b), (III-a), (III-b) and (IV):

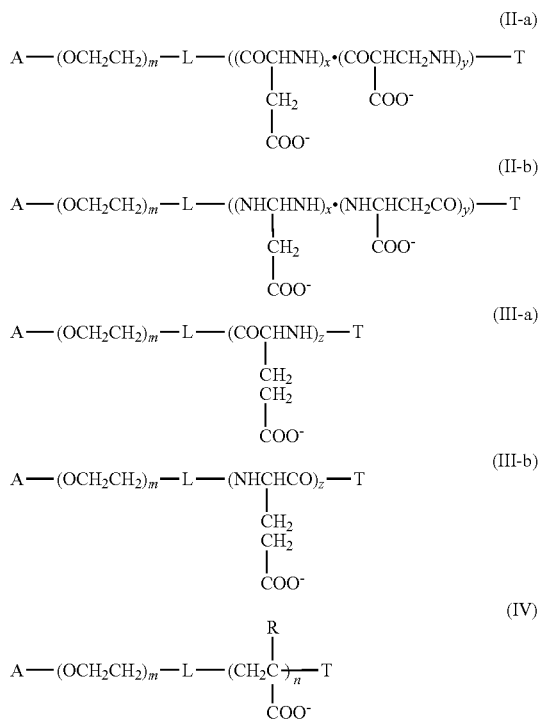

wherein in the above formulae,
each symbol is independently selected,
A represents hydrogen or a substituted or unsubstituted alkyl having up to 12 carbon atoms,
L represents a direct bond or a divalent linker,
T represents hydrogen, hydroxyl or —ZR in which Z represents a single bond, CO, O or NH, and R represents a hydrogen or methyl group,
m is an integer of 4-2,500,
n is an integer of 5-10,000,
x+y is an integer of 5-1,000, and
z is an integer of 5-1,000,
wherein up to 50% of the carboxylate ion group present can either have a counter ion derived from an alkali metal or from a carboxy ester residue;
and the contrast agent is a metal selected from the group consisting of gadolinium (Gd), europium (Eu), manganese (Mn), iron (Fe) and copper (Cu), the metal being in the form of a metal chelate with polydentate ligand of aminocarboxylic acid or phosphoric acid system, the aminocarboxylic acid or phosphoric acid system polydentate ligand being selected from the group consisting of ethylenediaminetetraacetic acid, diethylenetriaminepentaacetic acid, triethylenetetraminehexaacetic acid, ethylene glycol tetraminetetraacetic acid, tetraazacyclodecanetetraacetic acid, tetraazacyclododecanetriacetic acid, and tetraazacyclododecanetetraphosphoric acid.

7. The hybrid particle of claim 6, wherein L represents a linker and is selected from the group consisting of O, NH, CO and $X(CH_2)_pY$, where X represents OCO, OCONH, NHCO, NHCOO, NHCONH, CONH or COO, Y represents NH or CO, and p is an integer of 1-6.

8. The hybrid particle of claim 1, wherein average particle diameter in an aqueous dispersion of the particles is 50-600 nm as measured by dynamic light scattering method.

* * * * *